United States Patent [19]
Rice

[11] Patent Number: 4,646,339
[45] Date of Patent: Feb. 24, 1987

[54] ROTATING X-RAY MASK WITH SECTOR SLITS

[75] Inventor: Richard E. Rice, Arlington, Mass.

[73] Assignee: John K. Grady, Littleton, Mass.

[21] Appl. No.: 743,386

[22] Filed: Jun. 11, 1985

[51] Int. Cl.$^4$ .......................... G21K 5/10; G21K 1/04
[52] U.S. Cl. ...................................... 378/146; 378/160
[58] Field of Search .................. 378/146, 160; 358/111

[56] References Cited

U.S. PATENT DOCUMENTS

| | | | |
|---|---|---|---|
| 2,730,566 | 1/1956 | Bartow et al. | 378/146 |
| 3,780,291 | 12/1973 | Stein et al. | 378/146 |
| 4,315,146 | 2/1982 | Rubin | 378/146 |
| 4,403,338 | 9/1983 | Rubin | 378/146 |
| 4,404,591 | 9/1983 | Bonar | 378/146 |

OTHER PUBLICATIONS

Moore et al, "A Method to Absorb Scattered Radiation without Attenuation of the Primary Beam", Radiology, 120: 713–717, Sep. 1976.
Sorenson et al., "Investigations of Moving–Slit Radiology", Radiology, 120: 705–711, Sep. 1976.
Dick et al., "X-Ray Scatter Data for Diagnostic Radiology", Phys. Med. Biol., 1978, vol. 23, No. 6, 1076–1085.
Barnes et al., "The Design and Performance of a Scanning Multiple Slit Assembly", Med. Phys., 6(#) May/Jun. 1979, 197–204.
Sorenson et al., "Slit Radiography: Problems and Potential", SPIE, vol. 23, Application of Optical Instrumentation in Medicine VIII, 1980, pp. 240–243.
Bonar, "Dose Efficiency Improvement by Rotating Adjustable Apertures in an Image Intensifier X-Ray Diagnostic System", SPIE, vol. 314, Digital Radiography, 1981, pp. 81–87.
Yester et al., "Experimental Measurements of the Scatter Reductions... with a Scanning Multiple Slit Assembly", Med. Phys., 8(2) Mar./Apr. 1981, 158–162.
Johns et al., "Scattered Radiation in Fan Beam Imaging Systems", Med. Phys., 9(2), Mar./Apr. 1982, pp. 231–239.

Primary Examiner—Janice A. Howell
Attorney, Agent, or Firm—James H. Grover

[57] ABSTRACT

In an X-ray system with a rotating disk having sector slits transmitting fan shaped X-ray beams from a source through a subject to the image area of an X-ray receptor an improved ratio S/P of X-rays (S) scattered from the subject to primary rays (P) forming a true image of the subject at the image area is realized if the dimensions of the system fall within the following ranges of dimensionless ratios:

(1) DW/RL is less than 0.5;
(2) D/L is greater than 0.15;
(3) LS*N/WD is greater than 0.15 and less than 0.6
wherein
D is the distance of the disk from the X-ray source,
W is the width of the X-ray image area spanned by the narrow beams,
R is the radius of the disk,
L is the distance between the X-ray source and the receptor.
S* is the radially outermost slit width in the X-ray beam, and
N is the number of slits whose beams simultaneously intersect the outer edge of the image area.

7 Claims, 2 Drawing Figures

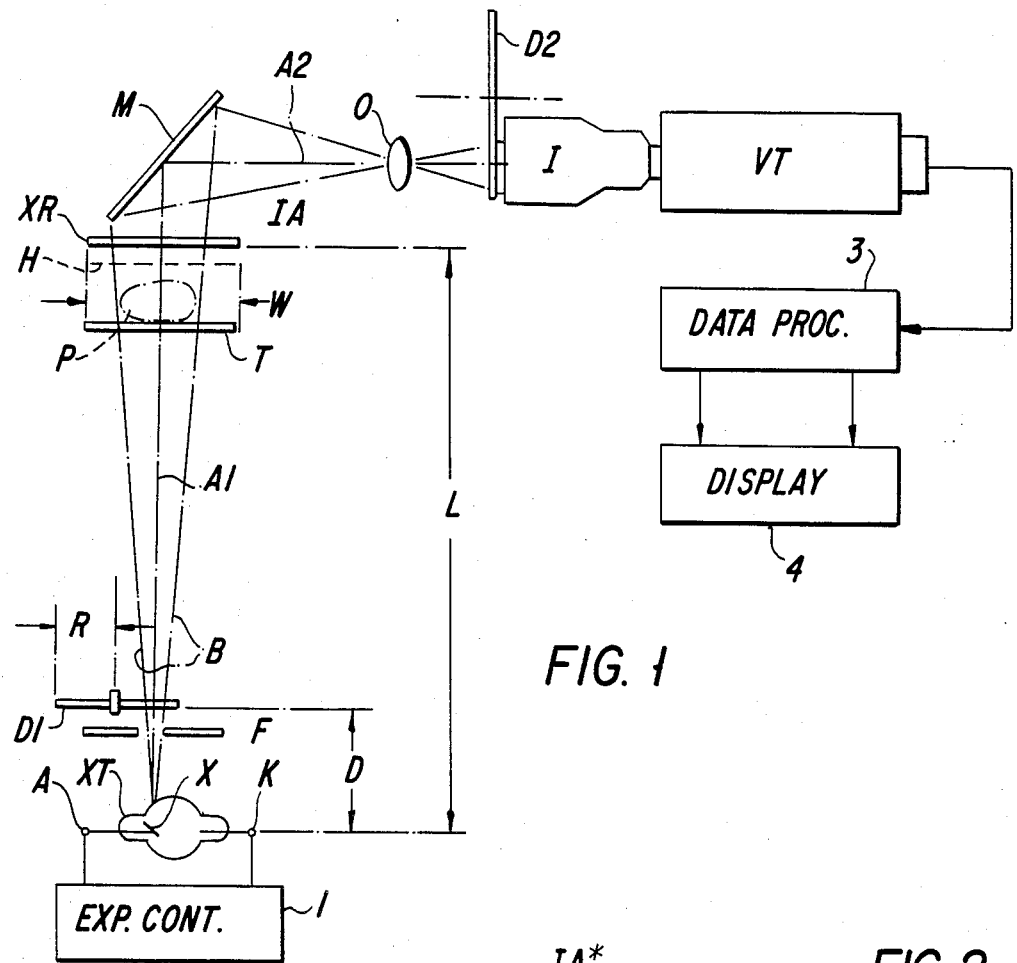

ROTATING X-RAY MASK WITH SECTOR SLITS

BACKGROUND OF THE INVENTION

In diagnostic X-ray equipment unwanted X-ray scatter can be reduced by interposing a rotating X-ray-opaque masking disk with X-ray transparent slits between an X-ray tube and the subject under examination. These slits are sectoral with their divergent long sides defined by radii from the axis of the disk, and serve to confine the X-rays to a fan shaped beam with a narrow sectoral cross section sweeping across the subject. Examples of slit radiography appear in U.S. Pat. Nos. 2,730,566 (Bartow), 4,315,146 (Rudin), and 4,404,591 (Bonar).

A disk using a single slit for each exposure sweep must be sector shaped for uniform exposure across the image area of the subject, but gives rise to non-uniform scatter of X-rays from the subject. Scatter is quantified by the ratio S/P of X-rays scattered from the subject to the primary rays forming the true image of the subject. This scatter-to-primary ratio S/P is not uniform over the image area scanned by a single sector-shaped beam, and may be non-uniform when disks with multiple slits are used to form a plurality of fan-shaped beams for each scan in a single X-ray exposure.

I have discovered that uniform exposure and uniform scatter-to-primary ratio S/P over an image area can be achieved with multiple sector slits provided certain limits of the geometric parameters of the system are observed. These limits are expressed in terms of dimensionless ratios and are thus general in scope.

SUMMARY OF THE INVENTION

According to the invention an X-ray system for examining a subject comprises an X-ray source directing a dimensioned beam of X-radiation through a subject position; an X-ray receptor with an image area in the beam beyond the subject position; and a rotating disk of radio-opaque material between the X-ray source and subject position, the disk having a plurality of spaced, sector-shaped X-ray slits in groups distributing X-radiation in narrow beams radially spanning the receptor image area and intersecting the outer edge of the image area while scanning the area during rotation of the disk; the dimensions of the system falling within the following ranges of dimensionless ratios:

(1) DW/RL is less than 0.5;
(2) D/L is greater than 0.15;
(3) LS*N/WD is greater than 0.15 and less than 0.6
wherein
  D is the distance of the disk from the X-ray source,
  W is the width of the X-ray image area spanned by the narrow beams,
  R is the radius of the disk,
  L is the distance between the X-ray source and the receptor.
  S* is the radially outermost slit width in the X-ray beam, and
  N is the number of slits whose beams simultaneously intersect the outer edge of the image area
whereby the quantity of scattered X-rays relative to X-rays forming an image at the receptor is minimized and X-ray scatter is substantially uniform throughout the image area.

Preferably the system includes an X-ray screening grid between the subject position and image area.

DRAWING

FIG. 1 is a diagrammatic view of an X-ray system with a sector slit disk according to the invention; and FIG. 2 is an enlarged, fragmental plan view of the sector slit disk of FIG. 1.

DESCRIPTION

The X-ray system of FIG. 1 consists of an X-ray tube XT with an anode A and a cathode K supplied with high voltage from an exposure control 1 to radiate X-rays in a divergent beam from a focal spot source X along an axis A1. From the source X the divergent X-ray beam passes through an image framing device F and an X-ray masking disk D1 along the axis A1 through the position P of a subject such as a human patient under examination on a table T, and thence through an X-ray screening grid H to an X-ray receptor XR. The term framing device identifies a stationary X-ray-opaque shield which defines an image area IA at the receptor XR and protects the patient from exposure to X rays outside the image area. A suitable grid is available as Type No. 9862 054 84101 from Philips Medical Systems, Shelton, Conn.

Although for the purposes of this invention the receptor XR may be an X ray sensitive film or other X-ray responsive medium, as shown the receptor is a scintillation screen producing a secondary, light image at its output area IA proportionate to received X-rays. The light image at the area IA is projected by lens optics O along a secondary, light axis A2 which is folded by a mirror M. The projected light image passes through a light masking disk D2, similar to and synchronized with disk D1, onto the input face of a light image intensifier I optically coupled to a video tube VT such as an image isocon which converts the intensified light image into electrical video signal data. The video signal is applied through a data processor 3 to utilization means such as a video display 4 or recorder.

The X-ray mask D1 shown in FIG. 2 is a disk of X-ray-opaque material such as tantalum, lead or uranium. Through the disk are X-ray transparent, sector shaped slits or apertures S whose long sides 6 are along radii from the center 5 of the disk D1. Each slit transmits a fan shaped beam radially spanning the image area IA as it scans laterally across the area. The slits diverge radially outwardly of the disk, and are spaced apart in a group G, for example, approximately 40 slits distributed through an angle of approximately 90°, 10 of which cover the radially outward edge E of the image area IA. The outer edge E intersects an arc S** traversed by the radially outermost effective ends of slits. The slits might extend further outwardly of this arc but without effect. The significant slit width S* is the width of the slit along the arc S** where the fan beam from each slit intersects the corners of the image area IA at its radially outward edge E. The width W of the image area IA is the dimension of the image area spanned radially by the fan beam from each slit. This width W is shown at its actual location at the image area in FIG. 1, but is shown in FIG. 2 in reduced size W* by a reverse projection IA* of the image IA area from the receptor plane to the plane of the disk D1. The projected image area IA* illustrates the same relation which the slits S have to the projected area IA* as the fan shaped beams they transmit have to the actual image area IA at the receptor R. In a disk of 10 centimeter radius the sector slits have a radially outer width near the disk periphery of 0.122 cm., for example.

The spacing of the slits is determined by the dimensionless ratios described hereafter. As the X-ray-opaque disk D1 rotates the sector slits S and their fan shaped beams scan laterally across the patient or other subject and across the image area.

In FIGS. 1 and 2 the disk D1 and other components of the X-ray system have dimensions which, according to the present invention, can be selected, despite the divergent sector shape of the X-ray transmissive slits S, to hold the scatter-to-primary ratio S/P, substantially and practically uniform throughout the image area.

A substantially uniform scatter-to-primary ratio can be realized if the X-ray system meets the limitations of following three dimensionless ratios:

(1) DW/RL is less than 0.5;
(2) D/L is greater than 0.15;
(3) LS*N/WD is greater than 0.15; and less than 0.6.

The parameters of these ratios are shown in FIGS. 1 and 2, wherein:

D is the distance of the X-ray opaque disk D1 from the X-ray source X.

W is the width of the X-ray image area spanned by the narrow fan beams,

R is the radius of the disk D1,

L is the distance between the X-ray source X and the receptor XR,

S* is the radially outermost slit width in the X-ray beam, and

N is the number, greater than one, of slits S whose beams simultaneously intersect the outer edge of the image area during scanning of the image area.

Typical values of the above parameters satisfying the dimensionless ratios are:

R is 10 cm.
D is 20 cm.
W is 20 cm.
L is 100 cm.
S* is 0.122 cm.
N is 10

When the parameters defining the dimensionless ratios are specified the X-ray transmission of the slit group G, and the spacing between sector slits are specified.

Preferably these ratios also satisfy the limits—

D/L is approximately 0.2
N is substantially equal to the numerical value of R in centimeters
LS*N/WD is between 0.3 and 0.5.

A principal problem with multiple slits arises from the scatter of X-rays from one fan shaped beam spreading into neighboring beams. This problem is significantly reduced by the presence of the grid H between the subject position P and the image area IA.

It should be understood that the present disclosure is for the purpose of illustration only and that this invention includes all modifications and equivalents which fall within the scope of the appended claims.

I claim:

1. An X-ray system for examining a subject comprising:

an X-ray source directing a fan-shaped beam of X-radiation through a subject position;

an X-ray receptor with an image area in the beam beyond the subject position; and a rotating disk of radio-opaque material between the X-ray source and subject position, the disk having a plurality of spaced, sector-shaped X-ray slits, whose sides are radial lines of the disk, in groups of more than one slit transmitting X-radiation in narrow moving beams radially spanning the receptor image area while scanning the image area during rotation of the disk;

the dimensions of the system falling within the following ranges of dimensionless ratios:

(1) DW/RL is less than 0.5;
(2) D/L is greater than 0.15;
(3) LS*N/WD is greater than 0.15 and less than 0.6 wherein

D is the distance of the disk from the X-ray source,

W is the width of the X-ray image area spanned by the narrow beams,

R is the radius of the disk,

L is the distance between the X-ray source and the receptor,

S* is the radially outermost slit width in the X-ray beam, and

N is the number, greater than one, of slits whose beams simultaneously intersect the outer edge of the image area, so that the quantity of scattered X-rays relative to X-rays forming an image at the receptor is minimized and X-ray scatter is substantially uniform throughout the image area.

2. A system according to claim 1 including a stationary X-ray screening grid between the subject position and the image area.

3. A system according to claim 1 wherein the X-ray receptor produces a light image and the system includes a light receptor and a rotating disk of light-opaque material and light-transparent sector slits between the X-ray receptor and light receptor.

4. A system according to claim 1 wherein the ratio D/L is greater than 0.15.

5. A system according to claim 1 wherein N is substantially equal to the numerical value of R in centimeters.

6. A system according to claim 1 wherein the ratio L/D is approximately 0.2.

7. A system according to claim 1 wherein the ratio LS*N/WD is between 0.3 and 0.5.

* * * * *

UNITED STATES PATENT AND TRADEMARK OFFICE
CERTIFICATE OF CORRECTION

PATENT NO. : 4,646,339

DATED : Feb. 24, 1987

INVENTOR(S) : Richard E. Rice

It is certified that error appears in the above–identified patent and that said Letters Patent are hereby corrected as shown below:

In claim 6, line 2, change the ratio "L/D" to

-- D/L --.

Signed and Sealed this

Third Day of May, 1988

Attest:

DONALD J. QUIGG

*Attesting Officer*    *Commissioner of Patents and Trademarks*